(12) United States Patent
Boeckh et al.

(10) Patent No.: US 7,531,186 B2
(45) Date of Patent: May 12, 2009

(54) TOPICAL FORMULATIONS COMPRISING 1-N-ARYLPYRAZOLE DERIVATIVES AND AMITRAZ

(75) Inventors: Albert Boeckh, Cumming, GA (US); Luiz Gustavo Cramer, Cumming, GA (US); Mark D. Soll, Alpharetta, GA (US)

(73) Assignee: Merial Limited, Duluth, GA (US)

( * ) Notice: Subject to any disclaimer, the term of this patent is extended or adjusted under 35 U.S.C. 154(b) by 809 days.

(21) Appl. No.: 10/783,459

(22) Filed: Feb. 20, 2004

(65) Prior Publication Data

US 2005/0137244 A1 Jun. 23, 2005

Related U.S. Application Data

(60) Provisional application No. 60/530,525, filed on Dec. 17, 2003.

(51) Int. Cl.
  *A01N 25/32* (2006.01)
(52) U.S. Cl. .................. 424/406; 424/405; 514/407; 514/636; 514/638
(58) Field of Classification Search ................ None
  See application file for complete search history.

(56) References Cited

U.S. PATENT DOCUMENTS

| | | | |
|---|---|---|---|
| 3,781,355 A | 12/1973 | Harrison et al. | |
| 3,864,497 A | 2/1975 | Harrison et al. | |
| 3,950,360 A | 4/1976 | Aoki et al. | |
| 4,199,569 A | 4/1980 | Chabala et al. | |
| 4,310,519 A | 1/1982 | Albers-Schonberg et al. | |
| 4,427,663 A | 1/1984 | Mrozik | |
| 4,855,317 A | 8/1989 | Gehret | |
| 4,859,657 A | 8/1989 | O'Sullivan et al. | |
| 4,871,719 A | 10/1989 | Maienfisch | |
| 4,874,749 A | 10/1989 | Mrozik | |
| 4,920,148 A | 4/1990 | Gehret | |
| 4,963,582 A | 10/1990 | Sato et al. | |
| 4,973,711 A | 11/1990 | Maienfisch | |
| 4,978,677 A | 12/1990 | Gehret | |
| 5,045,536 A | 9/1991 | Baker | |
| 5,055,596 A | 10/1991 | Baker et al. | |
| 5,077,308 A | 12/1991 | Blizzard | |
| 5,122,530 A | 6/1992 | Tomioka et al. | |
| 5,232,940 A | 8/1993 | Hatton et al. | |
| 5,236,938 A | 8/1993 | Huang et al. | |
| 5,567,429 A | 10/1996 | Senbo | |
| 5,576,429 A | 11/1996 | Johansson et al. | |
| 5,814,652 A | 9/1998 | Wu | |
| 5,885,607 A | 3/1999 | Jeannin | |
| 6,001,384 A | 12/1999 | Jeannin | |
| 6,010,710 A | 1/2000 | Etchegaray | |
| 6,083,519 A | 7/2000 | Jeannin | |
| 6,090,751 A | 7/2000 | Chen | |
| 6,096,329 A | 8/2000 | Jeannin | |
| 6,413,542 B1 | 7/2002 | Etchegaray et al. | |
| 6,426,333 B1 | 7/2002 | Huet et al. | |
| 6,482,425 B1 | 11/2002 | Huet et al. | |
| 6,538,013 B2 | 3/2003 | Goebel et al. | |
| 7,262,214 B2 * | 8/2007 | Soll et al. ................ | 514/407 |
| 2002/0090381 A1 | 7/2002 | Bottomly et al. | |
| 2003/0050327 A1 | 3/2003 | Huet et al. | |
| 2003/0166688 A1 | 9/2003 | Soll et al. | |

FOREIGN PATENT DOCUMENTS

| | | |
|---|---|---|
| CN | 1079776 A | 12/2003 |
| EP | A-295217 | 12/1988 |
| EP | A-352944 | 1/1990 |
| EP | 0 500 209 A1 | 8/1992 |
| WO | WO03/015519 A1 * | 2/2003 |

* cited by examiner

*Primary Examiner*—Neil Levy
(74) *Attorney, Agent, or Firm*—Judy Jarecki-Black; Merial Limited; Thomas Kowalski, Esq.

(57) ABSTRACT

The present invention provides for, inter alia, novel topical formulations comprising at least one 1-N-arypyrazole derivative and amitraz and to methods for treating, controlling, or preventing parasite infestations on mammals or birds The inventive formulations include spot-on, pour-on or spray formulations and may include a further ectoparasiticide, such as an IGR compound, an avermectin or milbemycin derivative, or a pyrethroid insecticides, and anthelmintics, such as benzimidazoles and imidazothiazoles. The inventive formulation provides a larger duration of parasite control at a faster rate of control. The inventive formula remains effective up to three months from the first application. Moreover, the inventive formulations prevent tick attachment to the animal, thereby providing protection against tick borne diseases. The ectoparasites which may be controlled, treated or prevented by the present invention includes ticks, fleas, mites, mange, lice, mosquitoes, flies and cattle grubs.

19 Claims, No Drawings

TOPICAL FORMULATIONS COMPRISING 1-N-ARYLPYRAZOLE DERIVATIVES AND AMITRAZ

RELATED APPLICATIONS

The application claim priority to provisional application U.S. Ser. No. 60/530,525, filed Dec. 17, 2003, herein incorporated by reference. Reference is also made to application U.S. Ser. No. 10/374,627 filed Feb. 26, 2003, entitled 1-N-arylpyrazole Derivatives in Prevention of Arthropod-Borne and Mosquito-Borne Diseases. This application and all applications and prior publications either therein or cited herein (including documents cited in the text or during prosecution) are expressly incorporated by reference.

FIELD OF THE INVENTION

This invention provide for, inter alia, novel topical formulations comprising at least one 1-N-arylpyrazole derivatives and amitraz and to methods for treating parasite infestations in mammals and birds by topically applying the inventive formulations to said mammals and birds. The inventive formulation exhibit activity against ectoparasites such as fleas and ticks, that is far superior than formulations comprising an 1-N-arypyrazole derivative alone, such as fipronil, thereby indicating synergy. This result is even more surprising given the fact that amitraz is not recognized in the field as a flea product.

BACKGROUND OF THE INVENTION

Parasitic diseases may be caused by either endoparasites or ectoparasites. As used herein endoparasites refer to those parasites living inside the body of the host, either within an organ (such as the stomach, lungs, heart, intestines, etc.) or simply under the skin. Ectoparasites are those parasites that live on the outer surface of the host but still draw nutrients from the host. Endoparasitic diseases may further be subdivided based on class of parasite involved in the infection. For example, endoparasitic diseases generally referred to as helminthiasis are due to infection of the host with parasitic worms known as helminths. Helminthiasis is a prevalent and serious worldwide economic problem involving infection of domesticated animals such as swine, sheep, horses, cattle, goats, dogs, cats, and poultry. Many of these infections, caused by the group of worms described as nematodes, cause diseases in various species of animals throughout the world. These diseases are frequently serious and can result in the death of the infected animal. The most common genera of nematodes infecting the animals referred to above include, but are not limited to, *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris,* and *Parascaris*. Many parasites are species specific (infect only one host) and most also have a preferred site of infection within the animal. Thus, *Haemonchus* and *Ostertagia* primarily infect the stomach while Nematodirus and Cooperia mostly attack the intestines. Other endoparasites reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Examples of endoparasites which infect animal and man include but are not limited to gastro-intestinal parasites of the genera *Ancylostoma, Necator, Ascaris, Strongyloides, Trichinella, Capillaria, Trichuris, Enterobius,* and the like. Other endoparasites which infect animal and man are found in the blood or in other organs. Examples of such parasites include but are not limited to filarial worms *Wuchereria, Brugia, Onchocerca,* and the like as well as extra-intestinal stages of the intestinal worms *Strongylides* and *Trichinella*. Ectoparasites which infest man and domestic animals include arthropods, such as ticks, fleas, mites, mosquitos, lice, and the like and infections by these parasites can result in transmission of serious and even fatal diseases.

Infestations by ectoparasitic arthropods including but not limited to ticks, mites, lice, stable flies, hornflies, blowflies, face flies, fleas, mosquitoes and the like are also a serious problem. Infection by these parasites results not only in loss of blood and skin lesions, but also can interfere with normal eating habits thus causing weight loss. Ectoparasitic infestations of a host can also result in transmission of serious diseases including but not limited to encephalitis, anaplasmosis, babesiosis, rocky mountain spotted fever, lyme disease, ehrlichiosis, West Nile virus, swine pox, malaria, yellow fever, and the like, many of which can be fatal to the host. Animals may be infected by several species of parasite at the same time since infection by one parasite may weaken the animal and make it more susceptible to infection by a second species of parasite.

Many of the compounds used in this invention are also active against household pests including but not limited to cockroach, *Blatella* sp., clothes moth, *Tineola* sp., carpet beetle, *Attagenus* sp. and the housefly *Musca domestica* and against *Solenopsis invicta* (imported fire ants), termites, and the like.

These compounds are furthermore useful against agricultural pests such as aphids (*Acyrthiosiphon* sp.) locusts, and boll weevils as well as against insect pest which attack stored grains such as *Tribolium* sp. and against immature stages of insects living on plant tissue. The compounds are also useful as a nematodicide for the control of soil nematodes, which may be agriculturally important.

Antiparasitic agents are also useful for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas, mosquitoes and the like. They are also effective in the treatment of parasitic infections of humans.

Various methods of formulating antiparasitical formulations are known in the art. These include oral formulations, baits, dietary supplements, powders, shampoos, etc. Formulations for localized topical applications of antiparasitical formulations are also known in the art. For example, pour-on solutions comprising 1-N-phenylpyrazole derivatives, such as fipronil, are known in the art and are described in, for example, U.S. Pat. No. 6,010,710, U.S. Pat. No. 6,413,542, U.S. Pat. No. 6,001,384, U.S. Pat. No. 6,413,542 as well as copending application Ser. No. 10/120,691, filed Apr. 11, 2002 and now allowed. Other methods of formulating antiparasitic agents include spot-on formulations or sprays.

Spot-on formulations are well known techniques for topically delivering an antiparasitic agent to a limited area of the host. For example, U.S. Pat. No. 5,045,536 describes such formulations for ectoparasites. Other spot-on formulations include U.S. Pat. No. 6,426,333 and U.S. Pat. No. 6,482,425 and application U.S. Ser. No. 10/155,397, now allowed and published as Publication No. U.S. 2003-0050327A1. Reference is also made to Publication No. U.S. 2003-166688A1. WO 01/957715 describes a method for controlling ectoparasites in small rodents as well as interrupting or preventing the diseases caused by arthropods or small rodents, which comprise applying topical formulations, such as spot-on compositions, to the skin, or hair of the rodents.

1-N-arylpyrazoles as a class of chemicals are well known in the art, as well as methods for their use in controlling parasites including insects, such as fleas, ticks, lice or mosquitoes in mammals, such as domesticated livestock or companion animals or birds, either alone or in combination with other pesticides such as insect growth regulators. See, e.g., EP-A-295,217, EP 295 177, EP-A-840-686, EP-A-352,944, WO 00/35844, WO 98/39972, U.S. Pat. Nos. 5,122,530 5,236,938, 5,232,940, 5,576,429 5,814,652, 5,567,429, 6,090,751 and 6,096,329 as well as Publication No. US 2002-90381-A1. See also copending applications U.S. Ser. Nos. 07/719,942; 08/933,016; 09/174,598; 08/863,182; and 08/863,692. The compounds of the families defined in these patents are extremely active and one of these compounds, 5-amino-3-cyano-1-(2,6-dichloro-4-trifluoromethylphenyl)-4-trifluoromethylsulfinylpyrazole, or fipronil, is particularly effective, but not exclusively effective, against fleas and ticks. The 1-arylpyrazoles exert their activity by being distributed through the sebaceous glands of the animal.

WO-A-87/3781, EP-A-295,117 and EP-A-500,209 describe a class of insecticides which are N-phenyl-pyrazole derivatives. These compounds are given as having activity against a very large number of parasites, including *Boophilus microplus*, fleas, ticks and lice in fields as varied as agriculture, public health and veterinary medicine. The general teaching of these documents indicates that these insecticidal compounds may be administered via different routes: oral, parenteral, percutaneous and topical routes. Topical administration comprises, in particular, oral formulations, baits, dietary supplements, skin solutions (pour-on or spot-on), sprays, drenches, baths, showers, jets, powders, greases, shampoos, creams, etc. The pour-on type skin solutions are designed for percutaneous administration. Example 9 of EP-A-295,117 and Example 29I of EP-A-500,209 describe a pour-on type skin solution containing 15% insecticide and 85% dimethyl sulphoxide, for percutaneous administration of the insecticide. 1-N-arylpyrazole derivatives are known in the art to prevent, treat or control ectoparasite infestation in mammals, such as cats, dogs and cattle.

Amitraz is known in the art as a pesticide and is used to control red spider mites, leaf mites, scale insects and aphids. In animals, amitraz is used to control tick, mites, and lice. Extoxnet http://ace.orst.edu/info/extonet/pips/amitraz.html. However, amitraz is not known in the art to treat fleas Amitraz belongs to the amidine chemical family and has the following structure:

Amitraz is described in U.S. Pat. No. 3,781,355 and U.S. Pat. No. 3,864,497.

Other compounds that are known in the art to present, treat or control endo- and ectoparasite infestation include milbemycin or avermectin derivatives. The avermectin and milbemycin series of compounds are potent anthelmintic and antiparasitic agents against a wide range of internal and external parasites. The compounds which belong to this series are either natural products or are semi-synthetic derivatives thereof. The structures of these two series of compounds are closely related and they both share a complex 16-membered macrocyclic lactone ring; however, the milbemycin do not contain the aglycone substituent in the 13-position of the lactone ring. The natural product avermectins are disclosed in U.S. Pat. No. 4,310,519 to Albers-Schonberg, et al., and the 22, 23-dihydro avermectin compounds are disclosed in Chabala, et al., U.S. Pat. No. 4,199,569. For a general discussion of avermectins, which include a discussion of their uses in humans and animals, see "Ivermectin and Abamectin," W. C. Campbell, ed., Springer-Verlag, New York (1989). Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874, 749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, and U.S. Pat. No. 4,920, 148.

Avermectins and milbemycins share the same common 16-membered macrocyclic lactone ring; however, milbemycins do not possess the disaccharide substituent on the 13-position of the lactone ring. While many avermectin compounds are known in the art, a representative structure of the class of compounds is as follows:

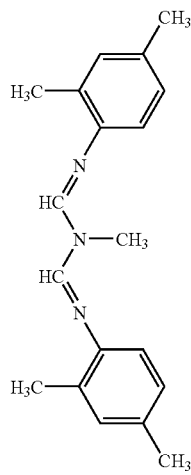

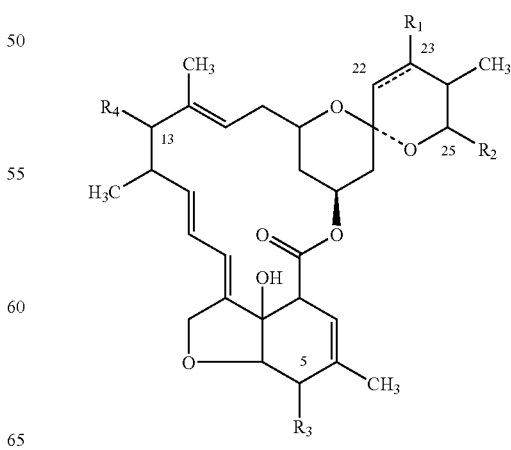

where the broken line indicates a single bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$ where $R_5$ is hydrogen or lower alkyl; and $R_4$ is hydrogen, hydroxy or

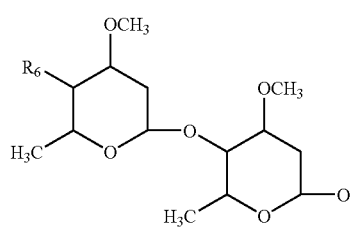

where $R_6$ is hydroxy, amino, mono- or di-lower alkylamino or lower alkanoylamino.

The structures of abamectin and ivermectin are as follows:

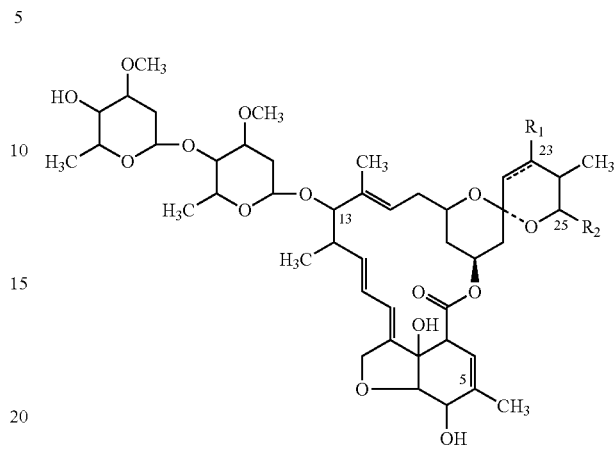

wherein for abamectin the broken line represents a double bond and $R_1$ is not present and for ivermectin the double bond represents a single bond and $R_1$ is hydrogen; and $R_2$ is isopropyl or sec-butyl.

The 4"-acetyl amino-5-ketoximino derivatives of avermectin B1a/B1b has the following structural formula:

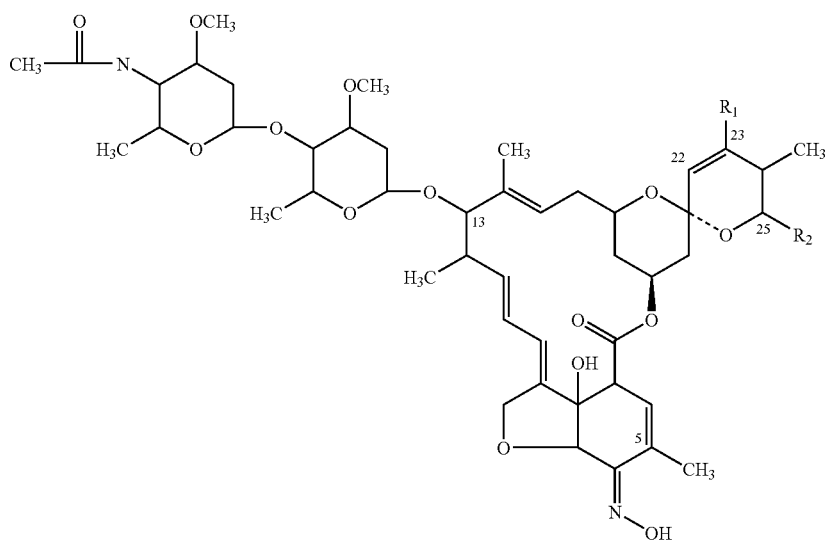

where $R_2$ is isopropyl or sec-butyl.

The avermectin products are generally prepared as a mixture of at least 80% of the compound where $R_2$ is sec-butyl and no more than 20% of the compound where $R_2$ is isopropyl.

The preferred compounds are avermectin B1a/B1b (abamectin), 22,23-dihydro avermectin B1a/B1b (ivermectin) and the 4"-acetylamino-5-ketoximino derivative of avermectin B1a/B1b. Both abamectin and ivermectin are approved as broad spectrum antiparasitic agents.

Other preferred avermectins, include emamectin, eprinomectin and doramectin. Doramectin is disclosed in U.S. Pat. No. 5,089,490 and EP 214 738. This compound has the following structure:

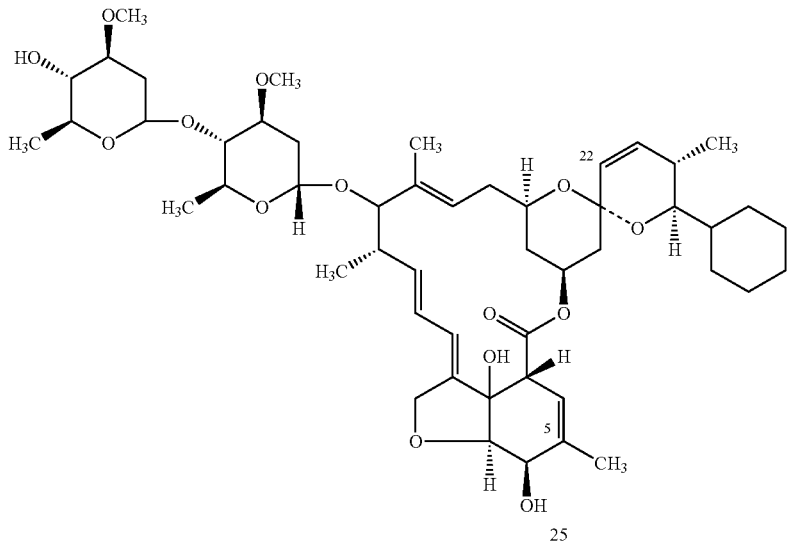

In the present formulations, ivermectin and eprinomectin are especially preferred.

A representative structure for a milbemycin is that for milbemycin α₁:

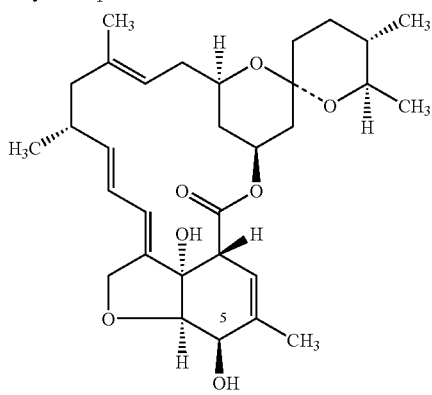

An especially preferred avermectin is moxidectin, whose structure is as follows:

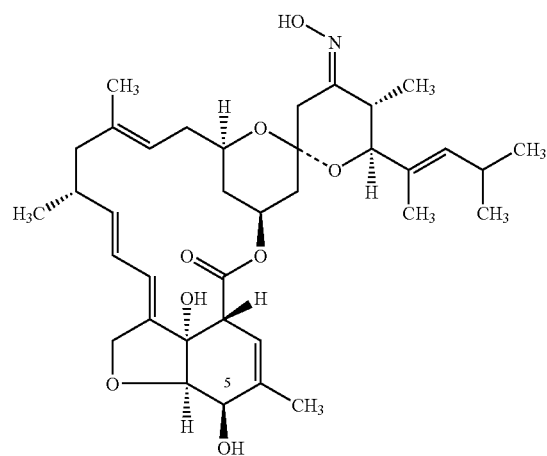

The compound is disclosed in U.S. Pat. No. 5,089,490.

Other classes of compound are known to treat endo-and ectoparasites. These classes include benzimidazoles, which are effective against tapeworms, lungworms and roundworms, imidazothiazoles, which are effective against roundworms, tapeworms and lungworms, and the pyrethroids. Examples of benzimidazoles inclcude albendazole (U.S. Pat. No. 3,915,986); fenbenzazole (U.S. Pat. No. 3,954,791), mebendazole (U.S. Pat. No. 3,657,261), oxibenzazole (U.S. Pat. No. 3,574,845) and triclabenzazole (U.S. Pat. No. 4,197,307). An example of an imidazothiazole is levamisole (U.S. Pat. No. 3,529,350).

The pyrethoids are a class of naturally occurring or synthetically derived insecticide. Their compounds are particularly effective against West Nile virus. Synthetic pyrethroids include pyrethrin I and pyrethrin II. Synthetic pyrethroids include permethrin (U.S. Pat. No. 4,113,968), resmethrin, and sumithrin (U.S. Pat. Nos. 3,934,023 and 2,348,930).

SUMMARY OF THE INVENTION

The present invention provides for, inter alia, novel topical formulations comprising at least one 1-N-arypyrazole derivative and amitraz and to methods for treating, controlling, or preventing parasite infestations on mammals or birds The inventive formulations include spot-on, pour-on or spray formulations and may include a further ectoparasiticide, such as an IGR compound, an avermectin or milbemycin derivative, or a pyrethroid insecticides, and anthelmintics, such as benzimidazoles and imidazothiazoles. The inventive formulation provides a larger duration of parasite control at a faster rate of control. The inventive formula remains effective up to three months from the first application. Moreover, the inventive formulations prevent tick attachment to the animal, thereby providing protection against tick borne diseases. The ectoparasites which may be controlled, treated or prevented by the present invention includes ticks, fleas, mites, mange, lice, mosquitoes, flies and cattle grubs.

More specifically, the present invention provides for, inter alia, a parasitical spot-on formulation, which comprises:
  a) an effective amount of an ectoparasitical combination comprising an 1-N-arylpyrazole derivative and amitraz;
  b) a pharmaceutical or veterinary acceptable liquid carrier vehicle;
  c) optionally, a crystallization inhibitor.

This invention further provides for a parasitical pour-on formulation, which comprises:
a) an effective amount of an ectoparasitical combination comprising an 1-N-arylpyrazole derivative and amitraz;
b) a pharmaceutical or veterinary acceptable liquid carrier vehicle;
c) optionally, a crystallization inhibitor; and
d) optionally, an antioxidant.

Also provided for in the present invention is a parasitical spray formulation, which comprises:
a) an effective amount of an ectoparasitical combination comprising an 1-N-arylpyrazole derivative and amitraz;
b) a pharmaceutical or veterinary acceptable liquid carrier vehicle.

A further embodiment of the present invention are spot-on, pour-on or spray formulations that further comprise at least one additional antiparasiticidal or anthelmintic agent, such as an IGR compound, a milbemycin or avermectin derivative, a pyrethroid, a benzimidazole, such as albendazole, fenbenzazole, mebendazole, oxibendazole, or triclobendazole, or a imidazothiazole, such as levamisole.

The present invention further provides for a method for preventing, eliminating or controlling parasites in a mammal or bird in need thereof or an environment where they reside, which comprises applying an effective amount of the inventive spot-on, pour-on or spray formulation to the mammal or bird. Animals include mammals, such as dog, cats, zebras and horses, and birds, such as chickens, turkeys and quail. Environments include animal houses, such as dog or cat bedding, horse stables and chicken litter.

DETAILED DESCRIPTION OF THE INVENTION

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents.

For convenience, certain terms employed in the Specification, Examples, and appended claims are collected here.

Definitions: As used herein, the term "comprising" in this disclosure can mean "including" or can have the meaning commonly given to the term "comprising" in U.S. Patent Law.

Preferred topical formulations include those formulations wherein the 1-arylpyrazol is a compound of the formula:

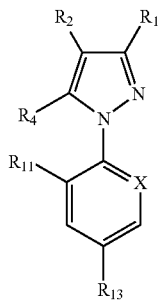

(I)

in which:
$R_1$ is a halogen atom, CN or alkyl;
$R_2$ is $S(O)_n R_3$ or 4,5-dicyanoimidazol-2-yl or haloalkyl;
$R_3$ is alkyl, alkenyl, alkynyl, haloalkyl, haloalkenyl or haloalkyl;
$R_4$ is hydrogen, halogen, $NR_5R_6$, $S(O)_m R_7$, $C(O)R_7$, $C(O)OR_7$, alkyl, haloalkyl, $OR_8$ or —N=$C(R_9)(R_{10})$ substituent;
$R_5$ and $R_6$ independently represent a hydrogen atom, alkyl, haloalkyl, C(O)alkyl, $S(O)_r CF_3$ or alkoxycarbonyl or $R_5$ and $R_6$ together may combine to form a ring of 5 to 7 members.
$R_7$ represents an alkyl or haloalkyl group;
$R_8$ represents an alkyl, haloalkyl or a hydrogen;
$R_9$ represents an alkyl or a hydrogen;
$R_{10}$ represents an optionally substituted aryl or an optionally substituted heteroaryl group;
$R_{11}$ and $R_{12}$ represent, independently of one another, hydrogen, halogen CN or $NO_2$;
$R_{13}$ represents a halogen atom or a haloalkyl, haloalkoxy, $S(O)_q CF_3$ or $SF_5$ group;
m, n, q and r represent, independently of one another, an integer equal to 0, 1 or 2;
X represents a trivalent nitrogen atom or a C—$R_{12}$, the three other valencies of the carbon atom forming part of the aromatic ring optionally with a pharmaceutically acceptable carrier or excipient.

A more preferred formulation is one wherein the 1-N-arylpyrazole is a compound of the formula:

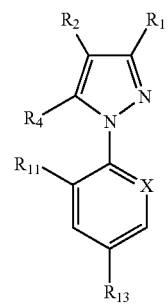

(I)

in which:
$R_1$ is a halogen atom, CN or methyl;
$R_2$ is $S(O)_n R_3$ or 4,5-dicyanoimidazol-2-yl or haloalkyl;
$R_3$ is alkyl, haloalkyl, haloalkenyl or haloalkynyl;
$R_4$ represents a hydrogen or halogen atom or an $NR_5R_6$, $S(O)_m R_7$, $C(O)R_7$ or $C(O)OR_7$, alkyl, haloalkyl or $OR_8$ or an —N=$C(R_9)(R_{10})$ group;
$R_5$ and $R_6$ independently represent a hydrogen atom or an alkyl, haloalkyl, C(O)alkyl, $S(O)_r CF_3$ or alkoxycarbonyl group or $R_5$ and $R_6$ together may form a ring of 5 to 7 members;
$R_7$ represents an alkyl or haloalkyl substituent;
$R_8$ represents an alkyl or haloalkyl or a hydrogen;
$R_9$ represents an alkyl or a hydrogen atom;
$R_{10}$ represents an optionally substituted aryl or an optionally substituted heteroaryl group;
$R_{11}$ and $R_{12}$ represent, independently of one another, hydrogen, halogen CN or $NO_2$;
$R_{13}$ represents a halogen atom or a haloalkyl, haloalkoxy, $S(O)_q CF_3$ or $SF_5$ group;
m, n, q and r represent, independently of one another, an integer equal to 0, 1 or 2;

X represents a trivalent nitrogen atom or a C—$R_{12}$, the three other valencies of the carbon atom forming part of the aromatic ring;

with the proviso that, when R is methyl, then either $R_3$ is haloalkyl, $R_4$ is $NH_2$, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl; and/or More preferably, this invention provides for a parasitical spot-on formulation wherein the 1-N-arylpyrazole in the ectoparasitical combination is a compound of the formula (I) wherein:

$R_1$ is a halogen atom, CN or methyl;

$R_2$ is $S(O)_nR_3$ or 4,5-dicyanoimidazol-2-yl or haloalkyl;

$R_3$ is $C_1$-$C_6$-alkyl or $C_1$-$C_6$-haloalkyl;

$R_4$ represents a hydrogen or halogen atom; or $NR_5R_6$, $S(O)_mR_7$, $C(O)R_7$ or $C(O)OR_7$, alkyl, haloalkyl or $OR_8$ or —N=C($R_9$) ($R_{10}$);

$R_5$ and $R_6$ independently represent a hydrogen atom or a $C_1$-$C_6$ alkyl, $C_1$-$C_6$-haloalkyl, $C(O)C_1$-$C_6$-alkyl, $S(O)_r$ $CF_3$, $C_1$-$C_6$-acyl or $C_1$-$C_6$-alkoxycarbonyl; $R_5$ and $R_6$ together may combine to form a ring of 5 to 7 members, which may include one or two divalent heteroatoms selected from the group consisting of oxygen or sulphur;

$R_7$ represents a $C_1$-$C_6$-alkyl or $C_1$-$C_6$-haloalkyl;

$R_8$ represents a $C_1$-$C_6$-alkyl or $C_1$-$C_6$-haloalkyl or a hydrogen atom;

$R_9$ represents a $C_1$-$C_6$-alkyl or a hydrogen atom;

$R_{10}$ represents an optionally substituted phenyl or optionally substituted heteroaryl group wherein the substituents are selected from the group consisting of halogen, OH, —O—$C_1$-$C_6$ alkyl, —S—$C_1$-$C_6$-alkyl, cyano or $C_1$-$C_6$-alkyl;

$R_{11}$ and $R_{12}$, independently of one another represent hydrogen, halogen, CN or $NO_2$;

$R_{13}$ represents a halogen, $C_1$-$C_6$-haloalkyl, $C_1$-$C_6$-haloalkoxy, $S(O)_qCl_3$ or $SF_5$ group; and, m, n, q and r independently of one another are 0, 1, or 2;

(b) the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethylene glycol monoethyl ether, monomethylacetamide, d ipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of ethanol, isopropanol or methanol; and (c) a crystallization inhibitor selected from the group consisting of an anionic surfactant, a cationic surfactant, a nonionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Especially preferred as spot-on formulations are those wherein the 1-N-arylpyrazole derivative in the ectoparasitical combination is a compound wherein the ring formed by the divalent alkylene substituent representing $R_5$ and $R_6$ and the nitrogen atom to which $R_5$ and $R_6$ are attached has 5, 6 or 7 members or wherein $R_1$ is CN, $R_3$ is $C_1$-$C_6$-haloalkyl, $R_4$ is $NH_2$, $R_{11}$, and $R_{12}$ are, independently of one another, hydrogen or halogen and $R_{13}$ is $C_1$-$C_6$-haloalkyl.

Most especially preferred 1-N-arylpyrazoles to be used in the inventive spot-on and pour-on formulations are:

(A) 5-amino-3-cyano-1-(2,6-dichloro-4-trifluoromethylphenyl)-4-trifluoromethylsulfinylpyrazole; or (B) 1-N-phenylpyrazole derivative of the formula:

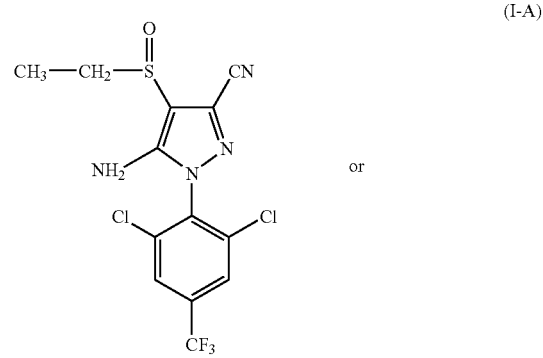

(I-A)

or

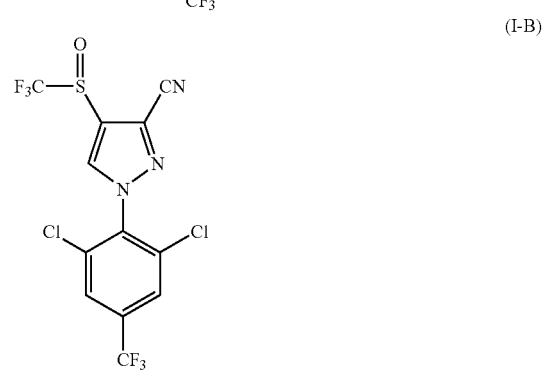

(I-B)

Other 1-N-arylpyrazole derivatives to be used in the formulation to the invention which are preferred are those of the formula (II)

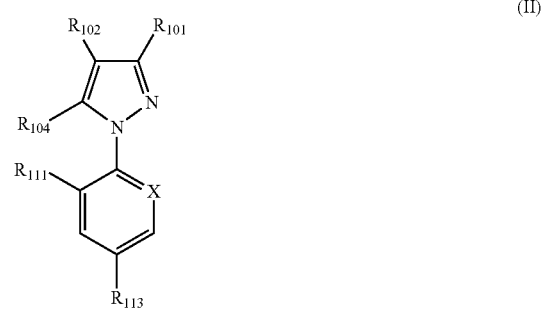

(II)

wherein:

$R_{101}$ is cyano, —C(O)alkyl, $C(S)NH_2$, alkyl, haloalkyl, C(=NOH)$NH_2$ or C(=$NNH_2$)$NH_2$;

$R_{102}$ is $S(O)_nR_{103}$, alkenyl, haloalkenyl, cycloalkyl, halocycloalkyl or alkynyl;

$R_{103}$ is alkyl, alkenyl, alkynyl, haloalkyl, haloalkenyl or haloalkynyl;

$R_{104}$ is —N=C($R_{105}$)-Z-$R_{106}$, —N=C($R_{105}$)—N ($R_{107}$)—$R_{108}$; or —N($R_{109}$)—C($R_{105}$)=$NR_{106}$;

$R_{105}$ is hydrogen; alkyl; or alkyl substituted by halogen, alkoxy, haloalkoxy or —S(O)$_m$$R_{105}$;

$R_{106}$ and $R_{107}$ each independently represent hydrogen, alkyl, alkenyl or alkynyl, or alkyl substituted by one or more halogen, alkoxy, haloalkoxy, amino, alkylamino, dialkylamino, cyano or —S(O)$_m$,R$_{115}$; or alkyl substituted by phenyl or pyridyl each of which is optionally substituted with one or more groups selected from halogen, nitro and alkyl group; or $R_{107}$ and $R_{108}$ may form together with the nitrogen to which they are attached a 3- to 7-membered ring which may additionally contain one or more heteroatoms selected from oxygen, nitrogen or sulfur;

$R_{108}$ is alkoxy, haloalkoxy, amino, alkylamino, dialkylamino, —C(O) R$_{114}$ or —S(O)$_n$R$_{110}$;

$R_{109}$, $R_{110}$ and $R_{114}$ are alkyl or haloalkyl;

$R_{111}$ and $R_{112}$ are independently selected from halogen, hydrogen, CN and NO$_2$ $R_{113}$ is selected from halogen, haloalkyl, haloalkoxy, —S(O)$_q$,CF$_3$, and —SF$_5$;

$R_{115}$ is alkyl or haloalkyl;

X is selected from nitrogen and C—R$_{112}$;

Z is O, S(O)$_a$'; or NR$_{107}$;

a', m', n' and q' are independently selected from 0, 1, and 2; and t' is 0, 1 or 2; and veterinary acceptable salts thereof.

Other preferred 1-N-arylpyrazole derivatives that may be included in the inventive formulations are those compounds of formula (III):

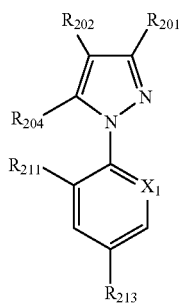

(III)

wherein:

$R_{201}$ is cyano, C(O)alkyl, C(S)NH$_2$, alkyl, C(=NOH)NH$_2$ or C(=NNH$_2$)NH$_2$;

$R_{202}$ is S(O)$_n$R$_{203}$, alkenyl, haloalkenyl, cycloalkyl, halocycloalkyl or alkynyl;

$R_{203}$ is alkyl, alkenyl, alkynyl, haloalkyl, haloalkenyl or haloalkynyl;

$R_{204}$ is —N(R$_{205}$)C(O)CR$_{206}$R$_{207}$R$_{208}$, —N(R$_{205}$)C(O) aryl, or —N(R$_{205}$)C(O)OR$_{207}$;

$R_{205}$ is alkyl, haloalkyl, cycloalkyl, halocycloalkyl, cycloalkylalkyl, halocycloalkylalkyl, alkoxyalkyl, haloalkoxyalkyl, alkenyl, haloalkenyl, alkynyl, haloalkynyl;

$R_{206}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkylsulfonyl, haloalkylsulfonyl, alkylamino, dialkylamino, haloalkylamino, di(haloalkyl)amino, cycloalkyloxy, halocycloalkyloxy, alkoxyalkoxy, haloalkoxyalkoxy, alkoxyalkoxyalkoxy, aryloxy, or arylalkoxy;

$R_{207}$ and $R_{208}$ are independently hydrogen, alkyl, haloalkyl, cycloalkyl, or halocycloalkyl; or $R_{207}$ and $R_{208}$ may form together with the carbon to which they are attached a 3- to 7-membered ring which additionally may contain one or more heteroatoms selected from nitrogen, oxygen and sulfur;

$X_1$ is selected from nitrogen and C—R$_{212}$;

$R_{211}$, and $R_{212}$ are independently selected from halogen, hydrogen, CN and NO$_2$;

$R_{213}$ is selected from halogen, haloalkyl, haloalkoxy, —S(O)$_k$CF$_3$, and —SF$_5$;

and h and k are independently selected from 0, 1, and 2;

and veterinary acceptable carrier, excipients and salts thereof.

A preferred class of compounds of formula (II) for use in the inventive formulation is those wherein:

$R_{103}$ is cyano or alkyl;

$R_{102}$ is S(O)$_n$,R$_{103}$;

$R_{103}$ is alkyl or haloalkyl;

$R_{104}$ is —N=C(R$_{105}$)-Z-R$_{106}$;

$R_{105}$ is hydrogen, alkyl or haloalkyl;

Z is O, S(O)$_a$'; or NR$_{107}$;

$R_{106}$ and $R_{107}$ are independently selected from hydrogen and unsubstituted or substituted alkyl; or $R_{106}$ and $R_{107}$ may form together with the nitrogen to which they are attached a 3- to 7-membered ring which may additionally contain one or more heteroatoms selected from oxygen, nitrogen or sulfur; X is selected from nitrogen and C—R$_{112}$;

$R_{111}$ and $R_{112}$ are independently selected from halogen, hydrogen, CN and NO$_2$;

$R_{113}$ is selected from halogen, haloalkyl, haloalkoxy, —S(O)$_q$,CF$_3$, and —SF$_5$;

a', n' and q' are independently selected from 0, 1, and 2.

Preferably, $R_{106}$ is alkyl which is substituted by one or more halogen, alkoxy, haloalkoxy, amino, alkylamino, dialkylamino, sulfide, sulfoxide, sulfone, or phenyl or pyridyl moieties of which each phenyl or pyridyl moiety is optionally substituted with one or more groups selected from halo, nitro, and alkyl.

Preferably, the 1-N-arylpyrazole has one or more of the following features:

$R_{101}$ is cyano;

$R_{104}$ is —N=C(R$_{105}$)-Z-R$_{106}$ and Z is —NR$_{107}$;

X is C—R$_{112}$; $R_{111}$ and $R_{112}$ represent a chlorine atom; and $R_{113}$ is CF$_3$, OCF$_3$, or —SF$_5$;

$R_{112}$ is —S(O)$_n$,CF$_3$ and n is 0, 1, or 2.

A further preferred class of 1-N-arylpyrazoles that may be included in the inventive formulations or approaches are those of formula II wherein:

$R_{101}$ is cyano or alkyl; $R_{104}$ is —N=C(R$_{105}$)-Z-R$_{106}$; and $R_{105}$ is hydrogen or C$_1$-C$_3$ alkyl.

The compounds of formula (II) preferably have one or more of the following features:

$R_{101}$ is cyano or methyl;

$R_{103}$ is halomethyl (preferably CF$_3$);

$R_{111}$ and $R_{112}$ each independently represent a halogen atom;

X is C—R$_{112}$;

$R_{113}$ is haloalkyl (preferably CF$_3$ haloalkoxy (preferably OCF$_3$), or —SF$_5$; or n' is 0, 1 or 2 (preferably 0 or 1).

A further preferred class of compounds of formula (II) for use in the inventive formulations and methods are those wherein:

$R_{101}$ is cyano;

$R_{102}$ is S(O)$_n$,R$_{103}$;

$R_{103}$ is halomethyl;

$R_{104}$ is —N=C(R$_{105}$)-Z-R$_{106}$;

Z is $NR_{107}$;

$R_{105}$ is hydrogen or alkyl;

$R_{106}$ and $R_{107}$ each independently represent hydrogen, alkyl, alkenyl or alkynyl; or alkyl substituted by one or more halogen, alkoxy, haloalkoxy, amino, alkylamino, dialkylamino, cyano or —$S(O)_mR_{15}$; or alkyl substituted by phenyl or pyridyl which rings are optionally substituted with one or more groups selected from halogen, nitro and alkyl;

X is selected from nitrogen and C—$R_{112}$;

$R_{106}$ and $R_{112}$ each independently represent a halogen atom; $R_{113}$ is selected from haloalkyl, haloalkoxy and —$SF_5$; $R_{115}$ is alkyl or haloalkyl; and m' and n' are independently selected from 0, 1, and 2.

A further preferred class of compounds of formula (II) is that wherein:

$R_{101}$ is cyano;

$R_{102}$ is $S(O)_n$,$CF_3$;

$R_{104}$ is —$N$=$C(R_{105})$-Z-$R_{106}$ or —$N$=$C(R_{05})$—$N(R_{107})$—$R_{108}$;

Z is $NR_{107}$;

$R_{105}$ is hydrogen or alkyl;

$R_{106}$ and $R_{107}$ each independently represent hydrogen, alkyl, alkenyl or alkynyl; or alkyl substituted by one or more halogen, alkoxy, haloalkoxy, amino, alkylamino, dialkylamino, cyano or —$S(O)R_{115}$; or methyl substituted by phenyl or pyridyl which rings are optionally substituted with one or more groups selected from halogen, nitro and alkyl;

$R_{108}$ is alkoxy, haloalkoxy, amino, alkylamino, dialkylamino or —$S(O)_tR_{110}$;

X is selected from nitrogen and C—$R_{112}$;

$R_{109}$, $R_{110}$ and $R_{114}$ independently represent alkyl or haloalkyl;

$R_{111}$ and $R_{112}$ each represent a chlorine atom;

$R_{113}$ is $CF_3$ or —$SF_5$; and m' and n' are 0, 1 or 2; and t' is 0 or 2.

A further preferred class of compounds of formula (II) are those wherein:

$R_{101}$ is cyano;

$R_{102}$ is $S(O)_{n1}CF_3$;

$R_{104}$ is —$N$=$C(R_{105})$-Z-$R_{106}$;

Z is $NR_{107}$;

$R_{105}$ is hydrogen or methyl;

$R_{106}$ and $R_{107}$ each independently represent hydrogen, alkyl, alkenyl or alkynyl; or alkyl substituted by one or more halogen, alkoxy, haloalkoxy, amino, alkylamino, dialkylamino, cyano or —$S(O)_m,R_{115}$; or alkyl substituted by phenyl or pyridyl which rings are optionally substituted with one or more groups selected from halogen, nitro and alkyl;

X is C—$R_{112}$ $R_{111}$ and $R_{112}$ each represent a chlorine atom;

$R_{113}$ is $CF_3$ or —$SF_5$;

m' is zero, one or two; and n' is 0 or 1.

A further preferred class of compounds of formula (II) is those wherein:

$R_{101}$ is cyano;

$R_{102}$ is $S(O)_n,CF_3$;

$R_{104}$ is —$N$=$C(R_{105})$-Z-$R_{106}$;

Z is $NR_{107}$;

$R_{105}$ and $R_{107}$ each represent a hydrogen atom;

$R_{106}$ is alkyl or haloalkyl;

X is C—$R_{112}$;

$R_{111}$ and $R_{112}$ each represent a chlorine atom;

$R_{113}$ is $CF_3$ or —$SF_5$; and n' is 0.

Compounds of formula (III) which are preferred according to the present invention are those wherein:

$R_{201}$ is cyano;

$R_{202}$ is $S(O)_hR_{203}$;

$R_{203}$ is alkyl or haloalkyl;

$R_{204}$ is —$N(R_{20\ 5})C(O)CR_{206}R_{207}R_{208}$;

$R_{205}$ is alkyl, haloalkyl, cycloalkyl, cycloalkylalkyl and halocycloalkylalkyl;

$R_{206}$ is alkoxy, haloalkoxy, or hydrogen;

$R_{207}$ and $R_{208}$ are independently hydrogen, alkyl, or haloalkyl; or $R_{207}$ and $R_{208}$ may form together with the carbon to which they are attached to a 3- to 7-membered ring which additionally may contain one or more heteroatoms selected from nitrogen, oxygen and sulfur;

$X_1$ is selected from nitrogen and C—$R_{212}$;

$R_{211}$ and $R_{212}$ are independently selected from halogen, hydrogen, CN and $NO_2$;

$R_{213}$ is selected from halogen, haloalkyl, haloalkoxy, —$S(O)_kCF_3$, and —$SF_5$;

and h and k are independently selected from 0, 1, and 2.

A preferred group of compounds of formula (III) is that wherein the ring which is formed by $R_{207}$ and $R_{208}$ contains one or more heteroatoms, more preferably one oxygen atom.

The compounds of formula (III) of the present invention preferably have one or more of the following features:

$R_{201}$ is cyano;

$R_{203}$ is halomethyl, preferably $CF_3$;

$R_{211}$ and $R_{212}$ are independently halogen;

$X_1$ is C—$R_{212}$;

$R_{213}$ is haloalkyl, haloalkoxy or —$SF_5$; or h is 0 or 1, or 2, preferably 0 or 1.

A preferred class of compounds that wherein $R_{204}$ is $N(R_{205})C(O)CR_{206}R_{207}R_{208}$.

Another preferred class of compounds that wherein $R_{204}$ is $N(R_{205})C(O)$aryl.

Another preferred class of compounds that wherein $R_{204}$ is $N(R_{205})C(O)OR_{207}$.

Preferably $R_{205}$ is $C_1$-$C_4$ alkyl, more preferably $C_1$-$C_2$ alkyl, most preferably methyl.

Preferably $R_{206}$ is alkoxy, most preferably methoxy, ethoxy or propoxy.

Preferably $R_{207}$ and $R_{208}$ are both hydrogen.

Another especially preferred group of 1-N-arylpyrazole derivatives is 4-thiocarbonylpyrazole derivatives of the formula:

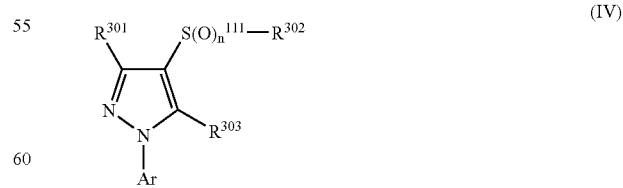

(IV)

in which $R^{301}$ is $H_2N$—$C(S)$—, $R^{302}$ is halogenoalkyl, halogenoalkenyl or halogenoalkynyl, $R^{303}$ is hydrogen, amino or one of the following groups:

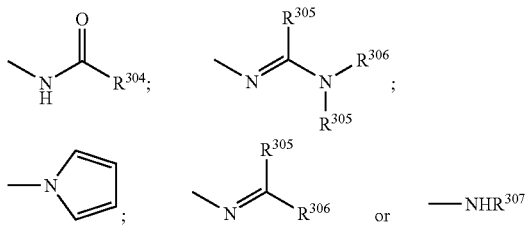

where
$R^{304}$ represents alkyl, halogenoalkyl, alkoxyalkyl or in each case optionally substituted phenyl or pyridyl,
$R^{305}$ represents hydrogen or alkyl,
$R^{306}$ represents hydrogen, alkyl or in each case optionally substituted phenyl or pyridyl and
$R^{307}$ represents alkyl, alkenyl, alkinyl, formyl, alkylcarbonyl, halogenoalkylcarbonyl or alkoxycarbonyl;
Ar represents in each case optionally substituted phenyl or pyridyl and n represents a number 0, 1 or 2.

Especially preferred derivatives of formula (IV) are those wherein
$R^{301}$ represents $H_2N$—C(S)—;
$R^{302}$ preferably represents $(C_1-C_6)$-halogenoalkyl having 1 to 12 halogen atoms; $(C_2-C_6)$-halogenoalkenyl having 1 to 8 halogen atoms or $(C_1-C_6)$-halogenoalkinyl having 1 to 6 halogen atoms;
$R^{303}$ preferably represents hydrogen, amino or one of the following groups:

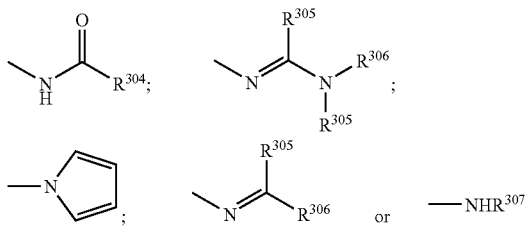

wherein:
$R^{304}$ represents $(C_1-C_6)$-alkyl, $(C_1-C_6)$-halogenoalkyl having 1 to 3 halogen atoms, $(C_1-C_6)$-alkoxy-$(C_1-C_6)$-alkyl, or represents phenyl or pyridyl, each of which is optionally monosubstituted to trisubstituted by identical or different substituents from the group consisting of cyano, nitro, halogen, $C_1$-$C_6$-alkyl, $C_1$-$C_6$-alkoxy, $C_1$-$C_6$-alkylthio, $C_1$-$C_4$-halogenoalkyl, $C_1$-$C_4$ halogenoalkoxy or $C_1$-$C_4$-halogenoalkylthio having in each case 1 to 5 halogen atoms,
$R^{305}$ represents hydrogen or $(C_1-C_6)$-alkyl,
$R^{306}$ represents hydrogen, $(C_1-C_6)$-alkyl, phenyl which is optionally monosubstituted to trisubstituted by identical or different substituents from the group consisting of cyano, nitro, halogen, $C_1$-$C_6$-alkyl, $C_1$-$C_6$-alkoxy, $C_1$-$C_6$-alkylthio, $C_1$-$C_4$-halogenoalkyl, $C_1$-$C_4$-halogenoalkoxy or $C_1$-$C_4$-halogenoalkylthio having in each case 1 to 5 halogen atoms or hydroxyl, or represents pyridyl which is substituted by cyano, nitro, halogen, $C_1$-$C_6$-alkyl, $C_1$-$C_6$-alkoxy, $C_1$-$C_6$-alkylthio, $C_1$-$C_4$-halogenoalkyl, $C_1$-$C_4$-halogenoalkoxy or $C_1$-$C_4$-halogenoalkylthio having in each case 1 to 5 halogen atoms, and $R^{307}$ represents $(C_1-C_6)$-alkyl, $(C_2-C_6)$-alkenyl, $(C_2-C_6)$-alkynyl, formyl, $(C_1-C_6)$-alkylcarbonyl, $(C_1-C_6)$-halogenoalkylcarbonyl having 1 to 6 halogen atoms or $(C_1-C_6)$-alkoxycarbonyl;
Ar preferably represents phenyl or pyridyl, each of which is optionally monosubstituted to trisubstituted by identical or different substituents from the group consisting of halogen halogeno$(C_1-C_6)$alkyl, halogeno$(C_1-C_6)$alkylthio, halogeno$(C_1-C_6)$alkoxy, $(C_1-C_6)$alkoxy, methoxy, hydrazine, $(C_1-C_6)$-dialkylhydrazino, amino, $(C_1-C_6)$alkylamino, di$(C_1-C_6)$alkylamino, $(C_1-C_6)$alkylimino, cyano, $(C_1-C_6)$alkylthio or the group

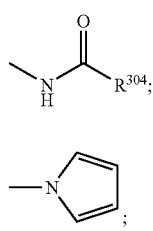

in which
$R^{308}$ and $R^{309}$ are identical or different and represent hydrogen or $(C_1-C_6)$-alkyl
$n^{111}$ preferably represents a number 0, 1 or 2.
$R^{301}$ represents $H_2N$—C(S)—;
$R^{302}$ particularly preferably represents $(C_1-C_4)$-halogenoalkyl having 1 or 9 identical or different halogen atoms from the group consisting of fluorine, chlorine and bromine, $(C_2-C_4)$-halogenoalkenyl having 1 to 5 identical or different halogen atoms from the group consisting of fluorine, chlorine or bromine or $(C_2-C_4)$-halogenoalkynyl having 1 to 5 identical or different halogen atoms from the group consisting of fluorine, chlorine and bromine; $R^{303}$ especially preferably represents hydrogen, amino or one of the following groups:

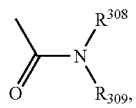

where
$R^{304}$ represents $(C_1-C_4)$-alkyl, $(C_1-C_4)$-halogenoalkyl having 1-3 halogen atoms, $(C_1-C_4)$-alkoxy$(C_1-C_2)$-alkyl, or phenyl which is optionally monosubstituted to trisubstituted by identical or different substituents from the group consisting of hydroxyl, cyano, nitro, halogen, $C_1$-$C_4$-alkyl, $C_1$-$C_4$-alkoxy, $(C_1$-$C_2$-halogenoalkyl, $C_1$-$C_2$-halogenoalkoxy or $C_1$-$C_2$-halogenoalkylthio having in each case 1 to 3 halogen atoms,
$R^{305}$ represents hydrogen or $(C_1-C_4)$-alkyl,
$R^{306}$ represents hydrogen, $(C_1-C_4)$-alkyl or phenyl which is optionally monosubstituted or disubstituted by identical or different substituents from the group consisting of hydroxyl, cyano, nitro, halogen, $C_1$-$C_4$-alkyl, $C_1$-$C_4$-alkoxy, $C_1$-$C_2$-halogenoalkyl, $C_1$-$C_2$ halogenoalkoxy or $C_1$-$C_2$ halogenoalkylthio having in each case 1 to 3 halogen atoms, in particular 4-hydroxy-3-methoxy-phenyl, and
$R^{307}$ represents $(C_1-C_4)$-alkyl, $(C_2-C_4)$-alkenyl, $(C_2-C_4)$-alkynyl, formyl, $(C_1-C_4)$-alkylcarbonyl, $(C_1-C_4,)$-halogenoalkylcarbonyl having 1 to 5 identical or different halogen atoms from the group consisting of fluorine, chlorine or bromine or $(C_1-C_4)$-alkoxycarbonyl;

Ar especially preferably represents phenyl or pyridyl, each of which is optionally monosubstituted to trisubstituted by identical or different substituents from the group consisting of fluorine, chlorine, trifluoromethyl, trifluoromethylthio, trifluoromethoxy, methoxy, hydrazine, dimethylhydrazino, amino, methylamino, dimethylamino, iminomethyl, cyano, methylthio or the group

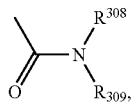

where
$R^{308}$ and $R^{309}$ are identical or different and represent hydrogen or $(C_1-C_4)$-alkyl;
$n^{111}$ especially preferably represents a number 0, 1 or 2.

Compounds of formula (IV) which are most preferably preferred are those where
$R^{301}$ represents $H_2N$—$C(S)$—;
$R^{302}$ most preferably represents one of the following groups:
—$CF_3$, —$CHF_2$—$CF_2$—$CH_3$, —$CF_3$—$CHF_2$, —$CF_2CHFCl$, —$CH_2$—$CF_3$, —$CH_2CF_2Cl$, —$CH_2$—$CF_2$—$CHF_2$, —$CF_2$—$CFC_1$-$CF_3$, —$C(Cl)(CF_3)$—$CF_2Cl$, —$C(Cl)(CF_3)$—$CHCl$—$CF_3$, —$C(CF_3)$=$CCl_2$ $R^{303}$ most preferably represents hydrogen, amino or one of the groups:

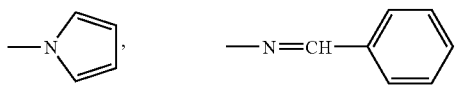

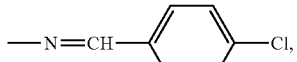

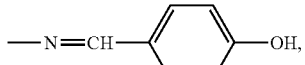

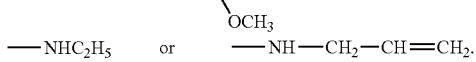

Ar most preferably represents
(1) phenyl which is disubstituted or trisubstituted by identical or different substituents, where fluorine or chlorine occupies the 2-position, trifluoromethyl the 4-position and fluorine, chlorine, cyano, methoxy, methylthio, trifluoromethyl, trifluoromethoxy, trifluoromethylthio or hydrazino the 6-position; or
(2) a 2-pyridyl substituent which is substituted in the 4-position by trifluoromethyl and in the 6-position by fluorine or chlorine.

$n^{111}$ most preferably represents one of the integers 0, 1 or 2.

A most especially preferred compound is one wherein $R^{302}$ is —$CF_3$, $R^{303}$ is amino, Ar is a phenyl which is trisubstituted and the substituents are a 2-position chloro group, a 4-position trifluoromethyl group and a 6-position chloro group, and $n^{111}$ is 1.

Especially preferred compounds are those of the formulae.

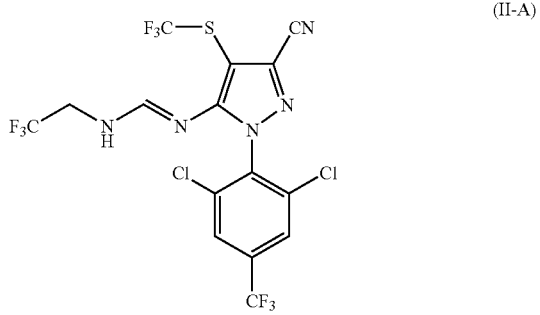

(II-A)

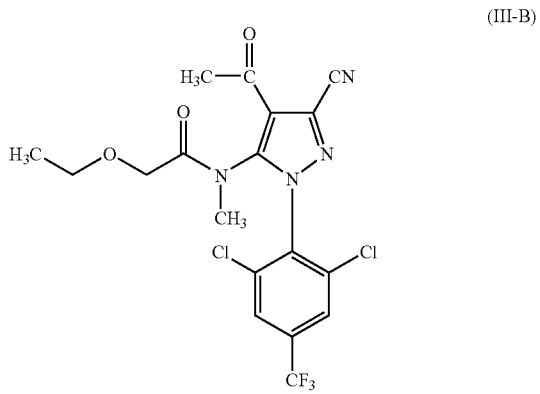

(III-B)

Other preferred 1-N-arylpyrazoles include the following compounds:

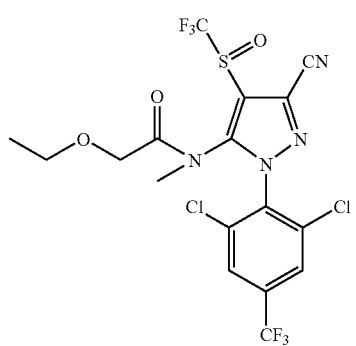

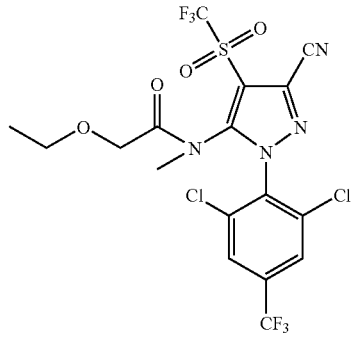

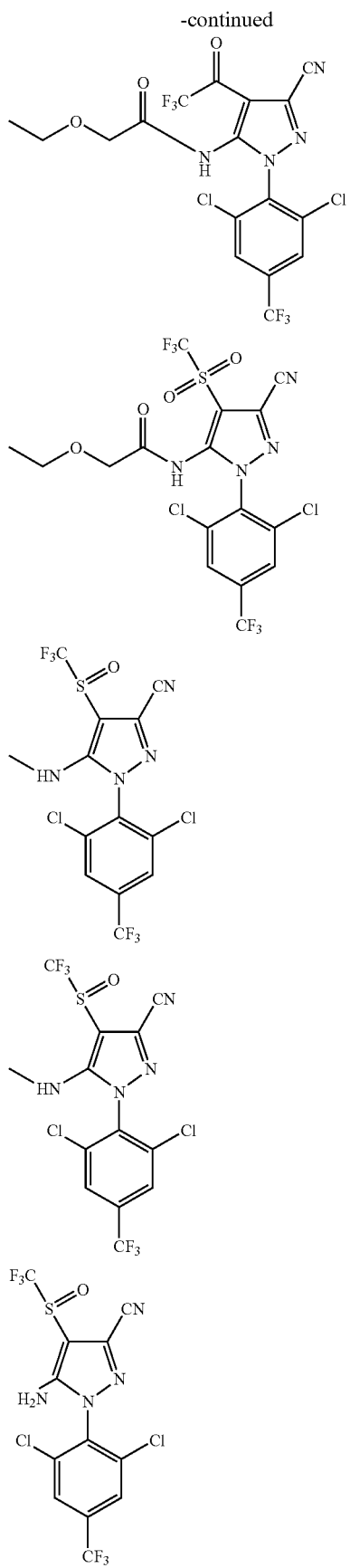
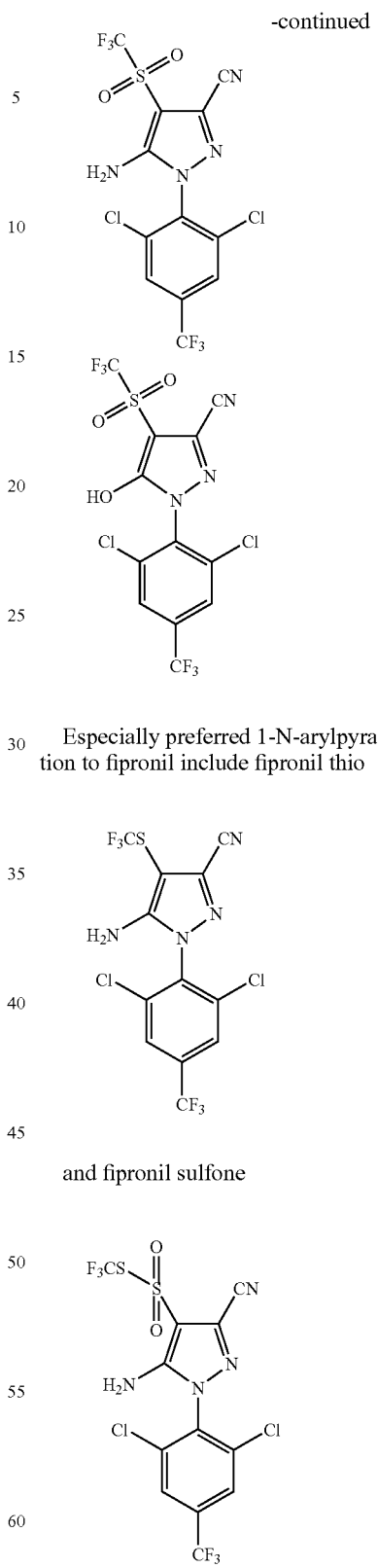
Especially preferred 1-N-arylpyrazoles derivative in addition to fipronil include fipronil thio
and fipronil sulfone
In addition to the patent discussing 1-N-arylpyrazoles derivatives discussed previously, one skilled in the art could make these compounds by adopting procedures described in DE 19928155, DE 19853560, WO 2000031043, DE 19650197, WO 9824769, U.S. Pat. No. 6,265,430, U.S. 2001007876, all of which are herein incorporated by reference.

The alkyl groups of the definition of the compounds (1) of the formula (I) generally comprise from 1 to 6 carbon atoms. The ring formed by $R_5$ and $R_6$ and the nitrogen atom to which they are attached is generally a 5-, 6- or 7-membered ring.

Unless otherwise specified, alkyl and alkoxy groups are generally lower alkyl and alkoxy groups, that is having from one to six carbon atoms, preferably from one to four carbon atoms. Generally, the haloalkyl, haloalkoxy and alkylamino groups have from one to four carbon atoms. The haloalkyl and haloalkoxy groups can bear one or more halogen atoms; preferred groups of this type include —$CF_3$ and —$OCF_3$. Cycloalkyl groups generally have from 3 to 6 carbon atoms, preferably from 3 to 5 carbon atoms, and may be substituted by one or more halogen atoms. Alkenyl, haloalkenyl, alkynyl, and haloalkynyl groups generally contain from 3 to 5 carbon atoms. By the term aryl is generally meant phenyl, pyridyl, furyl, and thiophenyl, each of which is optionally substituted by one or more halogen, alkyl, haloalkyl, nitro, alkoxy, haloalkoxy, hydroxy, amino, alkylamino or dialkylamino. In compounds of formulae (1) to (III), by the term substituted alkyl is meant alkyl which is substituted by, for example, one or more halogen, alkoxy, haloalkoxy, amino, alkylamino, dialkylamino, cyano or —$S(O)_mR_{115}$; or alkyl substituted by phenyl or pyridyl each of which is optionally substituted with one or more groups selected from halogen, nitro and alkyl; wherein $R_{115}$ is alkyl or haloalkyl and m is zero, one or two. Preferably in compounds of formula (I), alkyl groups are generally substituted by from one to five halogen atoms, preferably from one to three halogen atoms. Chlorine and fluorine atoms are preferred.

Compounds of formula wherein $R_{104}$ is —N=C($R_{105}$)-Z-$R_{106}$, Z is $NR_{107}$ and $R_{106}$ represent a hydrogen atom may exist as the tautomeric double bond isomer form —NH—C($R_{105}$)=N—$R_{107}$. It is to be understood that both such forms are embraced by the present invention.

In compounds of formula (III) the following examples of substituents are provided:

An example of cycloalkylalkyl is cyclopropylmethyl; an example of cycloalkoxy is cyclopropyloxy;

An example of alkoxyalkyl is $CH_3OCH_2$—;

An example of alkoxyalkoxy is $CH_3OCH_2O$—;

An example of alkoxyalkoxyalkoxy is $CH_3OCH_2OCH_2O$—;

An example of aryloxy is the phenoxy group; and

An example of the arylalkoxy group is benzyloxy or 2-phenylethoxy.

Generally, in dialkylamino or di(haloalkyl)amino groups, the alkyl and haloalkyl groups on nitrogen may be chosen independently of one another.

A preferred class of compounds of formula (I) comprises the compounds such that $R_1$ is CN, $R_3$ is haloalkyl, $R_4$ is $NH_2$, $R_{11}$ and $R_{12}$ are, independently of one another, a halogen atom and $R_{13}$ is haloalkyl. Preferably still, X is C—$R_{12}$. A compound of formula (I) which is very particularly preferred in the invention is 5-amino-3-cyano-1-(2,6-dichloro-4-trifluoromethylphenyl)-4-trifluoromethylsulfinylpyrazole or fipronil.

Compounds of formulae (I)-(III) can be prepared according to one or other of the processes described in Patent Applications WO 87/3781, 93/6089 and 94/21606, and 00/59862 or European Patent Application 295,117 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

As discussed above, amitraz is well known in the art and can be obtained from commercial source.

IGR compounds are another class of insecticides or acaricides, which are provided for in the bait formulations in this invention. Compounds belonging to this group are well known to the practitioner and represent a wide range of different chemical classes. These compounds all act by interfering with the development or growth of the insect pests. Compounds with an ovicidal and/or larvicidal effect on the immature stages of various ectoparasites are already known, for example from U.S. Pat. No. 5,439,924. Among these compounds described are those IGR compounds which act either by blocking the development of the immature stages (eggs and larvae) into adult stages, or by inhibiting the synthesis of chitin. Insect growth regulators are described, for example, in U.S. Pat. No. 3,748,356; U.S. Pat. No. 3,818,047; U.S. Pat. No. 4,225,598; U.S. Pat. No. 4,798,837; and U.S. Pat. No. 4,751,225, as well as in EP 179,022 or U.K. 2,140, 010. French Patent No. A-2,713,889 generally describes an IGR combination comprising at least one compound with juvenile hormone activity and chitin synthesis inhibitors, with at least one of three N-arylpyrazole compounds, in particular fipronil, to control many harmful insects belonging to very varied orders.

Examples of IGR compounds which may be used in this invention include compounds which mimic juvenile hormones, in particular:
 azadirchtin (Agridyne)
 diofenolan (Novartis)
 fenoxycarb (Novartis)
 hydroprene (Novartis)
 kinoprene (Novartis)
 methoprene (Novartis)
 pyriproxyfen (Sumitomo/Mgk)
 tetrahydroazadirachtin (Agridyne)
 4-chloro-2-(2-chloro-2-methylpropyl)-5-(6-iodo-3-pyridylmethoxy)pyridizin-3(2H)-one and chitin-synthesis inhibitors, in particular:
 chlorfluazuron (Ishihara Sangyo)
 cyromazine (Novartis)
 diflubenzuron (Solvay Duphar)
 fluazuron (Novartis)
 flucycloxuron (Solvay Duphar)
 flufenoxuron (Cyanamid)
 hexaflumuron (Dow Elanco)
 lufenuron (Novartis)
 tebufenozide (Rohm & Haas)
 teflubenzuron (Cyanamid)
 triflumuron (Bayer).

These compounds are defined by their international common name (The Pesticide Manual, $10^{th}$ edition, 1994, Ed. Clive Tomlin, Great Britain).

Chitin-synthesis inhibitors also include compounds such as 1-(2,6-difluorobenzoyl)-3-(2-fluoro-4-((trifluoromethyl)) phenylurea, 1-(2,6-difluorobenzoyl)-3-(2-fluoro-4-(1,1,2,2-tetrafluoroethoxy))phenylurea and 1-(2,6-difluorobenzoyl)-3-(2-fluoro-4-trifluoro-methyl)phenylurea. Novaluron (Isagro, Italian company) is also an example of an IGR compound.

Preferred IGR compounds include methoprenes, pyriproxyfens, hydroprene, cyromazine, lufenuron, 1-(2,6-difluorobenzoyl)-3-(2-fluoro-4-(trifluoromethyl)phenylurea and novaluron.

Other class compounds which maybe combined with the inventive ectoparasitical combination include avermectin and milbemycin derivatives, pyrethroids, benzamidazoles and imidazoles. Preferred avermectins or milbemycins include doramectin, enamectin, abamectin, eprinomectin, ivermectin, selamectin, moxidectin and milbemycin oxime. Preferred pyrethroids include the pyrethrins, permethrin, resmethrin and sumithrin. Preferred benzimidazole include albendazole, fenbenazole, mebendazole, oxibendazole and triclabendazole. A preferred imidazoleothiazole is levamisole. The amount of these compounds to be included with the inventive ectoparasitical combination depends on the type of animal and the degree of infestation. The amounts of these compounds are easily determined by one skilled in the art. Representative amounts include 0.001 mg/kg to 100 mg/kg, with the avermectins having preferred range of 0.001 mg/kg to 10 mg/kg and the other classes from 0.1 mg/kg to 100 mg/kg.

Administration of the inventive formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of animal, mammal or bird, and the environment where it resides. It is well within the skill level of the practitioner to determine a specific administration period for a particular situation. This invention contemplates a method for permanently combating a parasite in an environment in which the animal is subjected to strong parasitic pressure where the administration is at a frequency far below a daily administration in this case. For example, it is preferable for the treatment according to the invention to be carried out monthly on mammals, such as on dogs and on cats.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host. The compounds may be administered continuously, particularly for prophylaxis, by known methods. Generally, a dose of from about 0.001 to about 10 mg per kg of body weight given as a single dose or in divided doses for a period of from 1 to 5 days will be satisfactory but, of course, there can be instance where higher or lower dosage ranges are indicated and such are within the scope of this specific administration period for a particular situation. This invention contemplates a method for combating mosquitoes in an environment in which the animal is subjected to strong mosquito pressure where the administration is at a frequency far below a daily administration in this case. For example, it is preferable for the treatment according to the invention to be carried out monthly on dogs and on cats and or birds.

Spot-on and pour-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host. The compounds may be administered continuously, particularly for prophylaxis, by known methods. Generally, a dose of from about 0.001 to about 100 mg per kg body weight of 1-N-arylpyrazole and 0.01 to about 100 mg/kg of amitraz given as a single dose or in divided doses for a period of from 1 to 5 days will be satisfactory but, of course, there can be instance where higher or lower dosage ranges are indicated and such are within the scope of this invention. It is well within the routine skill of the practitioner to determine a particular dosing regimen for a specific host and parasite.

Preferably, a single formulation containing the 1-N-arylpyrazole derivative is in a substantially liquid carrier and is in a form which makes possible a single application or an application repeated a small number of times. The formulation will be administered to the animal over a highly localized region of the animal, preferably between the two shoulders. It is well within the routine skill of the practitioner to determine a particular dosing regimen for a specific host and parasite. Most preferably, this localized region has a surface area of less than 10 cm$^2$, especially between 5 and 10 cm$^2$ area. Remarkably, it has been discovered that such a formulation is highly effective against both the targeted parasites.

The treatment is preferably carried out so as to administer to the host, on a single occasion, a dose containing between about 0.001 and about 100 mg/kg of a compound of formula (II).

The amount of compounds of 1-N-aylpyrazole for animals which are small in size is preferably greater than about 0.01 mg and in a particularly preferred way between about 1 and about 50 mg/kg of weight of animal.

It also may be preferable to use controlled-release formulations.

This invention also provides for a method for cleaning the coats and the skin of animals by removal of the parasites which are present and of their waste and excreta. The animals treated thus exhibit a coat which is more pleasing to the eye and more pleasant to the touch.

The invention also relates to such a method with a therapeutic aim intended for the treatment and prevention of parasitoses having pathogenic consequences.

In another preferred embodiment this provides for a composition for combating fleas in small mammals, in particular dogs and cats, characterized in that it contains at least one of formula (II) as defined above.

The formulations of the present invention provide for the topical administration of a concentrated solution, suspension, microemulsion or emulsion for intermittent application to a spot on the animal, generally between the two shoulders (solution of spot-on type). It has been discovered that the inventive formulations are especially active against parasites when the formulations are applied to animals, such as mammals, especially dogs, cats, sheep, pigs, cattle and horses and birds, especially chickens, turkeys and quails. The ectoparasitical combination can advantageously be present in this formulation in a proportion of about 1 to about 20%, preferably of about 5 to about 15% (percentages as weight by volume=W/V). The liquid carrier vehicle comprises a pharmaceutically or veterinary acceptable organic solvent and optionally an organic cosolvent.

Also contemplated are the pharmaceutically or veterinary acceptable acid or base salts, where applicable, of the active compounds provided for herein. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tartaric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

The organic solvent for the liquid carrier vehicle will preferably have a dielectric constant of between about 10 and about 35, preferably between about 20 and about 30, the content of this solvent in the overall composition preferably representing the remainder to 100% of the composition. It is well within the skill level of the practitioner to select a suitable solvent on the basis of these parameters.

The organic cosolvent for the liquid carrier vehicle will preferably have a boiling point of less than about 100° C., preferably of less than about 80° C., and will have a dielectric constant of between about 10 and about 40, preferably between about 20 and about 30; this cosolvent can advantageously be present in the composition according to a weight/weight (W/W) ratio with respect to the solvent of between about 1/15 and about 1/2; the cosolvent is volatile in order to act in particular as drying promoter and is miscible with water and/or with the solvent. Again, it is well within the skill level of the practitioner to select a suitable solvent on the basis of these parameters.

The organic solvent for the liquid carrier includes the commonly acceptable organic solvents known in the formulation art. These solvents may be found, for example, in Remington Pharmaceutical Science, 16$^{th}$ Edition (1986). These solvents include, for example, acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as $C_8$-$C_{10}$ caprylic/capric triglyceride (Estasan or Miglyol 812), oleic acid or propylene glycol.

The liquid carrier may also comprise a microemulsion. Microemulsions are also well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. The oily phase preferably comprises triglycerides and more preferably medium-chain triglycerides, for example $C_8$-$C_{10}$ caprylic/capric triglyceride. The oily phase will represent, in particular, from about 2 to about 15%, more particularly from about 7 to about 10%, preferably from about 8 to about 9%, V/V of the microemulsion.

The aqueous phase includes, for example water or glycol derivatives, such as propylene glycol, glycol ethers, polyethylene glycols or glycerol. Propylene glycol, diethylene glycol monoethyl ether and dipropylene glycol monoethyl ether are especially preferred. Generally, the aqueous phase will represent a proportion from about 1 to about 4% V/V in the microemulsion.

Surfactants for the microemulsion include diethylene glycol monoethyl ether, dipropyelene glycol monomethyl ether, polyglycolysed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation.

The cosurfactant to surfactant ratio will preferably be from about 1/7 to about 1/2. There will preferably be from about 25 to about 75% V/V of surfactant and from about 10 to about 55% V/V of cosurfactant in the microemulsion.

Likewise, the co-solvents are also well known to a practitioner in the formulation art. Preferred co-solvents are those which is a promoter of drying and include, for example, absolute ethanol, isopropanol (2-propanol) or methanol.

The crystallization inhibitor can in particular be present in a proportion of about 1 to about 20% (W/V), preferably of about 5 to about 15%. The inhibitor preferably corresponds to the test in which 0.3 ml of a solution comprising 10% (W/V) of the compound of formula (I) in the liquid carrier and 10% of the inhibitor are deposited on a glass slide at 20° C. and allowed to stand for 24 hours. The slide is then observed with the naked eye. Acceptable inhibitors are those whose addition provides for few or no crystals, and in particular less than 10 crystals, preferably 0 crystals.

Although this is not preferred, the formulation can optionally comprise water, in particular in a proportion of 0 to about 30% (volume by volume V/V), in particular of 0 to about 5%.

The formulation can also comprise an antioxidizing agent intended to inhibit oxidation in air, this agent being in particular present in a proportion of about 0.005 to about 1% (W/V), preferably of about 0.01 to about 0.05%.

Crystallization inhibitors which can be used in the invention include:

polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, or preferably a mixture of at least two of the compounds listed above.

In a particularly preferred embodiment, a crystallization inhibitor pair will be used. Such pairs include, for example, the combination of a film-forming agent of polymeric type and of a surface-active agent. These agents will be selected in particular from the compounds mentioned above as crystallization inhibitor.

Particularly preferred film-forming agents of polymeric type include:

the various grades of polyvinylpyrrolidone, polyvinyl alcohols, and copolymers of vinyl acetate and of vinylpyrrolidone.

Especially preferred surface-active agents, include those made of non-ionic surfactants, preferably polyoxyethylenated esters of sorbitan and in particular the various grades of polysorbate, for example Polysorbate 80.

The film-forming agent and the surface-active agent can in particular be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the fur, that is to say without a tendency towards sticking or towards a sticky appearance, despite the high concentration of active material.

Particularly preferred antioxidizing agents are those conventional in the art and include, for example, butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied can be of the order of about 0.3 to about 1 ml, preferably of the order of about 0.5 ml, for cats and of the order of about 0.3 to about 5 ml for dogs, depending on the weight of the animal.

The pour-on solutions according to the invention, which are advantageously oily, generally comprise a diluent or vehicle and also a solvent (organic solvent) for the compound of formula (II) if the latter is not soluble in the diluent. Low concentrations of from about 0.05 to about 10% weight/volume, more particularly from about 0.1 to about 2%, are preferred. Optimally, the value is between about 0.25 and about 1.5%, in particular in the region of about 1%.

Organic solvents which can be used in the inventive pour-on solutions, mention may be made in particular of: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol and diethyl phthalate, or a mixture of at least two of these solvents.

As vehicle or diluent for the inventive pour-on solutions, mention may be made in particular of:

plant oils such as soybean oil, groundnut oil, castor oil, corn oil, cotton oil, olive oil, grape seed oil, sunflower oil, etc.; mineral oils such as petrolatum, paraffin, silicone, etc.; aliphatic or cyclic hydrocarbons or alternatively, for example, medium-chain ($C_8$ to $C_{12}$ in particular) triglycerides.

An emollient and/or spreading and/or film-forming agent will preferably be added, this agent being selected in particular from:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils, in particular polydimethylsiloxane (PDMS) oils, for example those containing silanol functionalities, or a 45V2 oil, anionic surfactants such as alkaline stearates, in particular sodium, potassium or ammonium stearates; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, amine salts of formula $N^+R'R''R'''$ in which the radicals R are optionally hydroxylated hydrocarbon radicals; octadecylamine hydrochloride is among the cationic surfactants which can be used, nonionic surfactants such as sorbitan esters, which are optionally polyoxyethylenated, in particular polysorbate 80, polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as the substituted lauryl compounds of betaine;

or a mixture of at least two of these agents.

The solvent will be used in proportion with the concentration of the compound II and its solubility in this solvent.

The emollient is preferably used in a proportion of from about 0.1 to about 10%, in particular from about 0.25 to about 5%, by volume.

This invention further provides for parasitical spray formulations which comprise:

a) an effective amount of an ectoparasitical combination comprising 1-N-arylpyrazole derivative and amitraz; and b) a pharmaceutical or veterinary acceptable liquid carrier vehicle.

Preferred carrier vehicles include isopropanol, ethanol, methanol, acetone, ether(s), propylene glycol, polyethylene glycol, glycol formal, DGME and DMSO.

EXAMPLES

The following non-limiting examples illustrate the invention:

Example 1

The following formulation according to the present invention was prepared by conventional techniques:

| Ingredient | Amount (% w/v) |
| --- | --- |
| fipronil | 10.0 |
| amitraz | 5.0 |
| ethanol | 10.0 |
| polyvidone | 5.0 |
| polysorbate 80 | 5.0 |
| butylated hydroxyanisole | 0.02 |
| butylated hydroxytoluene | 0.01 |
| diethyleneglycol monoethyl ether | QS 100 |

Example 2

The following formulation according to the present invention was prepared by conventional techniques:

| Ingredient | Amount (% w/v) |
| --- | --- |
| fipronil | 10.0 |
| amitraz | 15.0 |
| ethanol | 10.0 |
| polyvidone | 5.0 |
| polysorbate 80 | 5.0 |
| butylated hydroxyanisole | 0.02 |
| butylated hydroxytoluene | 0.01 |
| diethyleneglycol monoethyl ether | QS 100 |

Example 3

The following formulation according to the present invention was prepared by conventional techniques:

| Ingredient | Amount (% w/v) |
| --- | --- |
| fipronil | 10.0 |
| amitraz | 12.0 |
| ethanol | 10.0 |
| polyvidone | 5.0 |
| polysorbate 80 | 5.0 |
| butylated hydroxyanisole | 0.02 |
| butylated hydroxytoluene | 0.01 |
| diethyleneglycol monoethyl ether | QS 100 |

Comparative Example 4

The following formulation not according to the present invention was prepared by conventional techniques:

| Ingredient | Amount (% w/v) |
| --- | --- |
| fipronil | 10.0 |
| ethanol | 10.0 |
| polyvidone | 5.0 |
| polysorbate 80 | 5.0 |
| butylated hydroxyanisole | 0.02 |
| butylated hydroxytoluene | 0.01 |
| diethyleneglycol monoethyl ether | QS 100 |

Example 5

The duration of the efficacy of the formulation of Example 3 (according to the present invention) was compared with the formulation of Comparative Example 4 against ticks on dogs. The results are presented below:

| Duration of Efficacy against *Rhipicephalus sanguineus* ticks on dogs. (% efficacy at 48-hour counts) | | | | | | | | |
| --- | --- | --- | --- | --- | --- | --- | --- | --- |
| Days after Treatment | | | | | | | | |
| 2 | 9 | 16 | 23 | 30 | 37 | 44 | 51 | 58 |
| Fipronil 10% | | | | | | | | |
| 99.1% | 100.0% | 100.0% | 100.0% | 100.0% | 87.6% | 74.8% | 66.2% | 36.3% |
| Fipronil 10% + Amitraz 12% | | | | | | | | |
| 99.1% | 100.0% | 100.0% | 100.0% | 100.0% | 100.0% | 94.8% | 84.1% | 83.5% |

As can be seen the formulation according to the present invention remained effective for a far longer period than fipronil alone.

Example 6

The speed of the efficacy of the formulation of Example 3 (according to the present invention) was compared with the formulation of Comparative Example 4 against ticks on dogs. The results are presented below:

Speed of efficacy against *Rhipicephalus sanguineus* ticks on dogs.
(Efficacy counts were performed 6 hours after each weekly infestation)

| | Days after Treatment | | | | | | |
|---|---|---|---|---|---|---|---|
| | 0 | 7 | 14 | 21 | 28 | 35 | 42 |
| Fipronil 10% | — | 98.6% | 91.0% | 21.3% | 18.8% | 7.9% | — |
| Fipronil 10% + Amitraz 12% | 23.8% | 100.0% | 100.0% | 95.6% | 95.2% | 52.2% | 7.6% |

As can be seen the formulation according to the present invention exhibit a faster rate of efficacy than a formulation comprising fipronil alone.

Example 7

The duration of the efficacy of the formulation of Example 3 (according to the present invention) was compared with the formulation of Comparative Example 4 against fleas on dogs. The results are presented below:

Duration of efficacy against fleas
(% efficacy against fleas measured 24 hours after each weekly infestation)

| | Days after Treatment | | | | | |
|---|---|---|---|---|---|---|
| | 2 | 23 | 30 | 37 | 44 | 51 |
| Fipronil 10% | 100.0% | 100.0% | 99.0% | 93.8% | 69.4% | 41.48% |
| Fipronil 10% + Amitraz 12% | 100.0% | 100.0% | 100.0% | 98.4% | 96.3% | 94.6% |

As can be seen the formulation according to the present invention remained effective for a far longer period of time than a formulation comprising fipronil alone. This enhanced efficacy is surprising since amitraz is not known in the art to be used in treating flea infestations on mammals and birds.

The above description is intended to be illustrative and not limiting. Various changes or modifications in the embodiments described herein may occur to those skilled in the art. These changes can be made without departing from the scope or spirit of the invention.

The invention claimed is:

1. A veterinary parasitical spot-on formulation, which comprises:
   a) a veterinary parasiticidally effective amount of an ectoparasitical combination consisting essentially of fipronil and amitraz; and
   b) a pharmaceutical or veterinary acceptable liquid carrier spot-on formulation vehicle for applying the formulation to a localized region on an animal wherein the localized region is less than 10 cm$^2$ and wherein the formulation optionally includes a crystallization inhibitor.

2. The parasitical spot-on formulation according to claim 1, wherein
   the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate fatty acid esters, and a mixture of at least two of these solvents and the cosolvent is selected from the group consisting of ethanol, isopropanol and methanol
   the crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, and acrylic derivatives, and a mixture of these crystallization inhibitors.

3. The parasitical spot-on composition according to claim 2, wherein the formulation further comprises an antioxidant.

4. The parasitical spot-on composition according to claim 3, wherein the antioxidant is selected from the group consisting of butylated hydroxyanisole, butylated hydroxytoluene, ascorbic acid, sodium metabisulphite, propyl gallate and sodium thiosulphate.

5. The parasitical spot-on formulation according to claim 2, wherein water is present in a proportion of from 0 to about 30% v/v.

6. The parasitical spot-on formulation according to claim 2, wherein the crystallization inhibitor is present in an amount from about 1 to about 20% w/v.

7. The parasitical spot-on formulation according to claim 1 which comprises a crystallization inhibitor.

8. The parasitical spot-on formulation according to claim 2, wherein
   the anionic surfactant is alkaline stearates, sodium abietate; alkyl sulphates; sodium dodecylbenzenesulphonate, sodium dioctylsulphosuccinate, and fatty acids;
   the cationic surfactant is water-soluble quaternary ammonium salts of formula $N^+R'R''R'''R''''Y^-$ in which the radicals R independently are hydrocarbon radicals, optionally hydroxylated, and $Y^-$ is an anion of a strong acid;

the amine salt is an amine salt of N⁺R'R"R'" in which the radicals R independently are optionally hydroxylated hydrocarbon radicals;

the non-ionic surfactant is optionally polyoxyethylenated sorbitan esters, polyoxyethylenated alkyl ethers, polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide; and the amphoteric surfactant is lauryl-substituted betaine compounds.

9. The parasitical spot-on formulation according to claim 3, wherein the crystallization inhibitor is a crystallization inhibitor system comprising a polymeric film-forming agent and a surfactant.

10. The parasitical spot-on formulation according to claim 3, wherein the polymeric film-forming agent is polyvinylpyrrolidone, polyvinyl alcohols, or a copolymer of vinyl acetate and polyvinylpyrrolidone and the surfactant is a non-ionic surfactant.

11. The parasitical spot-on formulation according to claim 10, wherein the crystallization inhibitor system is a mixture of polyvinylpyrrolidone and polyoxethylene (20) sorbitan mono-oleate.

12. The parasiticidal formulation of any one of claims 1-11, wherein the composition is prepared by mixing its constituents.

13. The parasiticidal formulation of claim 12 wherein each of the fipronil and amitraz is an active material, the vehicle includes a solvent as to each active material, and the mixing of the constituents of the compositions comprises each active material being mixed in the solvent as to each active material.

14. The parasiticidal formulation of claim 13 wherein there are at least two solvents.

15. The parasiticidal formulation of claim of claim 14 which includes an ester.

16. The parasiticidal formulation of claim 15 wherein the carrier includes isopropanol, ethanol, methanol, acetone, ether(s), propylene glycol, polyethylene glycol, glycol formal, di-ethylene glycol monomethyl ether (DGME), or dimethyl sulfoxide (DMSO).

17. The parasiticidal formulation of claim 1 wherein the vehicle includes DMSO.

18. The parasiticidal formulation of claim 1 wherein the vehicle includes polyvinylpyrrolidone.

19. A parasitical spot-on formulation of claim 1, which comprises:
   a) an effective amount of an ectoparasitical combination consisting of fipronil and amitraz;
   b) wherein the carrier includes di-ethylene glycol monomethyl ether and ethanol; and
   c) optionally, a crystallization inhibitor.

* * * * *